United States Patent
Matsuzaki et al.

(10) Patent No.: US 7,160,306 B2
(45) Date of Patent: Jan. 9, 2007

(54) SURGICAL INSTRUMENTS AND A SET OF SURGICAL INSTRUMENTS FOR USE IN TREATMENT OF VERTEBRAL BODIES

(75) Inventors: Hiromi Matsuzaki, 33-6, Kamitakada 4-chome, Nakano-ku, Tokyo (JP); Yoshie Tominaga, Saitama (JP)

(73) Assignees: Pentax Corporation, Tokyo (JP); Hiromi Matsuzaki, Tokyo (JP)

( * ) Notice: Subject to any disclaimer, the term of this patent is extended or adjusted under 35 U.S.C. 154(b) by 376 days.

(21) Appl. No.: 10/309,881

(22) Filed: Dec. 5, 2002

(65) Prior Publication Data
US 2003/0109883 A1    Jun. 12, 2003

(30) Foreign Application Priority Data
Dec. 6, 2001 (JP) .............................. 2001-373441

(51) Int. Cl.
*A61F 5/00* (2006.01)
(52) U.S. Cl. ...................................................... 606/86
(58) Field of Classification Search ................ 606/53, 606/79, 83, 84, 86, 99, 85; 7/147, 170; 81/8.1, 81/20
See application file for complete search history.

(56) References Cited

U.S. PATENT DOCUMENTS

| | | | |
|---|---|---|---|
| 2,850,007 A | 9/1958 | Lingley | |
| 4,657,002 A | 4/1987 | Ray | |
| 4,985,031 A * | 1/1991 | Buss et al. | 606/82 |
| 5,108,404 A | 4/1992 | Scholten et al. | |
| 5,133,719 A | 7/1992 | Winston | |
| 5,163,939 A | 11/1992 | Winston | |
| 5,380,329 A | 1/1995 | Elia et al. | |
| 5,573,537 A | 11/1996 | Rogozinski | |
| 5,630,819 A | 5/1997 | Ashby et al. | |
| 5,713,736 A | 2/1998 | Heath et al. | |
| 5,910,315 A | 6/1999 | Stevenson et al. | |
| 5,972,015 A | 10/1999 | Scribner et al. | |
| 5,997,298 A | 12/1999 | Nowak | |
| 6,217,335 B1 | 4/2001 | Riitano et al. | |
| 6,241,734 B1 | 6/2001 | Scribner et al. | |

(Continued)

FOREIGN PATENT DOCUMENTS

EP    1060731    12/2000

(Continued)

*Primary Examiner*—Eduardo C. Robert
*Assistant Examiner*—Anu Ramana
(74) *Attorney, Agent, or Firm*—Greenblum & Bernstein, P.L.C.

(57) ABSTRACT

Various surgical instruments for use in the treatment of vertebral body compression fractures, used respectively for: widening a working path; reducing deformity; inserting a filler; and impacting a filler are provided. A set of surgical instruments including these instruments makes it possible to treat collapsed vertebral bodies easily and reliably are provided. The set includes a guide rod 1 (an instrument for widening a working path), a vertical elevator 2 (an instrument for reducing deformity), a horizontal elevator 3 (an instrument for reducing deformity), an inserter 4 (an instrument for inserting a filler), and an impactor 5 (an instrument for impacting a filler). The guide rod 1 is used for widening a path 93 formed in a collapsed vertebral body 91. The vertical elevator 2 is used for returning the upper anterior portion of the collapsed vertebral body 91 to a substantially original shape. The horizontal elevator 3 is used for returning the upper middle portion of the collapsed vertebral body 91 to a substantially original shape. The inserter 4 is used for inserting a filler into the reduced vertebral body 91. The impactor 5 is used for increasing the density of the filler inserted into the reduced vertebral body 91.

19 Claims, 12 Drawing Sheets

U.S. PATENT DOCUMENTS

| | | |
|---|---|---|
| 6,267,767 B1 | 7/2001 | Strobel et al. |
| 6,632,235 B1 * | 10/2003 | Weikel et al. ............... 606/192 |
| 6,679,886 B1 * | 1/2004 | Weikel et al. ................ 606/79 |
| 2002/0165612 A1 * | 11/2002 | Gerber et al. ............ 623/17.11 |

FOREIGN PATENT DOCUMENTS

| | | |
|---|---|---|
| EP | 888752 | 10/2002 |
| WO | 98/03119 | 1/1998 |
| WO | 00/54705 | 9/2000 |
| WO | 02/13700 | 2/2002 |
| WO | 02/ 13700 | 2/2002 |
| WO | 02/017794 | 3/2002 |
| WO | 02/19930 | 3/2002 |
| WO | 03/007853 | 1/2003 |
| WO | 03/022165 | 3/2003 |

\* cited by examiner (A)

(B)

(A)

(B)

(A)

(B)

(A)

(B)

(A)

(B)

(A)

(B)

SURGICAL INSTRUMENTS AND A SET OF SURGICAL INSTRUMENTS FOR USE IN TREATMENT OF VERTEBRAL BODIES

BACKGROUND OF THE INVENTION

1. Field of the Invention

This invention relates to surgical instruments for use in the treatment of vertebral bodies, and more particularly to surgical instruments used respectively for: widening a working path; reducing deformity; inserting a filler; and impacting the inserted filler, and to a set of surgical instruments comprised of these instruments.

2. Description of the Prior Art

Collapse of a vertebral body as a result of trauma or osteoporosis is referred to as a vertebral body compression fracture in the method that is known for the treatment of this kind of fracture, the collapsed vertebral body is repaired by filling the inside thereof with a filler through a vertebral arch using a transpedicular approach.

In this treatment method, a collapsed vertebral body is first returned to a substantially original shape, that is, a collapsed vertebral body is reduced, whereby a cavity is created therein. A filler such as a bone prosthesis is then inserted into the cavity to repair the vertebral body. This type of procedure is conventionally performed using an instrument such as a probe.

However, a problem exists with the use of this type of probe instrument in that since it is formed from a straight rod-shaped member, there is a case that the collapsed vertebral body can not be satisfactorily reduced.

Further, in the method using such a probe to reduce a collapsed vertebral body, an operator must take great care so as not to fracture a vertebral arch, especially small pedicles of the vertebral arch, thus requiring a high degree of mental and physical efforts.

SUMMARY OF THE INVENTION

It is therefore an object of the present invention to provide various surgical instruments and a set of surgical instruments for use in the treatment of vertebral body compression fractures, the use of which makes it possible to treat collapsed vertebral bodies easily and reliably. These instruments include: one for widening a working path; one for reducing deformity; one for inserting a filler; and one for impacting the inserted filler.

One aspect of the invention is directed to an instrument for use in the treatment of vertebral body compression fractures for widening a working path formed in at least a collapsed vertebral body, the instrument for widening a working path comprising a rod-shaped body having a distal end, a proximal end and a peripheral surface, wherein the distal end portion of the rod-shaped body is adapted to be inserted into the working path to increase its diameter. Using this instrument, it is possible to widen a working path formed in at least a vertebral body easily and reliably.

In the present invention, it is preferred that the distal end of the rod-shaped body has a rounded form, which makes it possible to prevent accidental damage to adjacent tissue during widening of the working path.

Further, the instrument is adapted to be used by being inserted into the working path, and it is preferred that the rod-shaped body has a scale for use in indicating a depth of insertion, the scale extending in a longitudinal direction of the rod-shaped body along the peripheral surface thereof. Provision of this scale enables a position of the distal end of the rod-shaped body within the vertebral body to be readily determined.

Furthermore, it is also preferred that the instrument further comprises a grip section which is fixedly provided on the proximal end of the rod-shaped body. Provision of this grip section facilitates operability of the instrument since an operator is able to retain a firm grip on the instrument when using it to widen a working path.

Another aspect of the invention is directed to an instrument for use in the treatment of vertebral body compression fractures for returning the upper portion of a collapsed vertebral body to a substantially original shape, the instrument for reducing deformity comprising: a rod-shaped main body having a distal end, a proximal end and a peripheral surface; and a pushing section provided on the distal end of the main body, the pushing section being inclined to the main body for pushing the upper portion of the vertebral body. Using this instrument, it is possible to return the upper portion of a collapsed vertebral body to a substantially original shape easily and reliably.

In the present invention, the pushing section preferably has a contact surface which comes into contact with the upper surface of the inside of the vertebral body. This contact surface makes it possible to perform reduction of the vertebral body more reliably. The contact surface is preferably formed with irregularities, which makes it possible to prevent or to suppress slippage of the contact surface against the upper surface of the inside of the vertebral body.

When the instrument is used for reducing the upper anterior portion of the vertebral body, the pushing section preferably has a distal end surface that functions as the contact surface. Also, when the instrument is used for reducing the upper middle portion of the vertebral body, the pushing section preferably has a peripheral surface, at least a part of which functions as the contact surface.

Further, the pushing section is preferably formed to have the following features: to be integral with the main body, so as to facilitate manufacture of the instrument; to be flat, so as to more reliably reduce the vertebral body; to form an inclined angle of between 5 to 30° between the pushing section and the main body, so as to reduce the vertebral body more easily and reliably within a broad range.

In the present invention, the instrument is adapted to be used by being inserted into the vertebral body through a working path formed in a vertebra, and the main body preferably has a scale for use in indicating a depth of insertion, the scale extending in a longitudinal direction of the main body along the peripheral surface thereof. Provision of this scale enables a position of the distal end of the pushing section within the vertebral body to be readily determined.

Preferably, the instrument further comprises a grip section which is fixedly provided on the proximal end of the main body, which facilitates operability of the instrument for reducing deformity since an operator is able to retain a firm grip on the instrument when using it to reduce deformity.

Also preferably, the instrument has a marker for indicating a direction in which the pushing section is inclined, which makes it possible to readily determine a direction in which the pushing section points within the vertebral body.

Still another aspect of the invention is directed to an instrument for use in the treatment of vertebral body compression fractures for inserting a filler into a reduced vertebral body, the instrument for inserting a filler comprising: a tubular body having a distal end, a proximal end and a peripheral surface, the tubular body having a lumen passing through from the proximal end to the distal end thereof; and an ejector bar which is to be inserted into the lumen of the tubular body to eject a filler filled in the lumen, the ejector bar having a distal end and a proximal end. By use of this instrument, it is possible to insert a filler into a reduced vertebral-body easily and reliably.

In the present invention, the distal end of the ejector bar preferably has a rounded form, which makes it possible to prevent accidental damage to adjacent tissue during insertion of the filler.

Also, the distal end of the ejector bar preferably projects outward from the distal end of the tubular body when the ejector bar is inserted into the tubular body, which makes it possible to effectively eject the filler from the lumen of the tubular body.

The ejector bar preferably has an ejector bar grip section which is fixedly provided on the proximal end of the ejector bar, which facilitates operability of the instrument for inserting a filler since an operator is able to retain a firm grip on the instrument when using it to insert a filler into the vertebral body.

In the present invention, the instrument is adapted to be used by being inserted into the vertebral body through a working path formed in a vertebra, and the tubular body preferably has a scale for use in indicating a depth of insertion, the scale extending in a longitudinal direction of the tubular body along the peripheral surface thereof. Provision of this scale enables a position of the distal end of the tubular body or that of the elector bar within the vertebral body to be readily determined.

The tubular body preferably has a tubular body grip section, the tubular body grip section being fixedly provided on the proximal end of the tubular body, which facilitates operability of the instrument for inserting a filler since an operator is able to retain a firm grip on the instrument when using it to insert a filler into the vertebral body.

The tubular body grip section preferably has a longitudinal middle portion extending in a circumferential direction, in which a recess is formed. This makes it possible for the operator to grip the tubular body grip section more firmly.

Further, the tubular body grip section preferably has an annular flange which is provided on its proximal end. This makes it possible for the operator to still more firmly grip the tubular body grip section.

Preferably, the internal diameter of the tubular body grip section is gradually increased toward its proximal end, which makes it possible to feed the filler into the lumen of the tubular body and to insert the ejector bar into the lumen of the tubular body more easily and reliably.

The filler is preferably a bone prosthesis, in which case the bone prosthesis is constituted from ceramic powders or calcium phosphate-based compound powders.

In a case that the filler is constituted from calcium phosphate-based compound powders, it will remain stable in a living body over a long-period of time.

Yet another aspect of the invention is directed to an instrument for use in the treatment of vertebral body compression fractures for impacting a filler inserted in a reduced vertebral body to a high-density, the instrument for impacting a filler comprising: a rod-shaped main body having a distal end, a proximal end and a peripheral surface; and a impacting section provided on the distal end of the main body for impacting the filler, the impacting section having a distal end. By use of this instrument, it is possible to increase a density of the filler inserted in the vertebral body easily and reliably.

In the present invention, the outer diameter of the impacting section is preferably gradually increased toward the distal end thereof, which enables an area of the impacting section in contact with the filler to be increased.

The impacting section preferably has a distal end surface formed with irregularities, which makes it possible for the impacting section to catch the filler effectively.

Also preferably, the impacting section is integrally formed with the main body, which facilitates manufacture of the instrument for impacting the inserted filler.

In the present invention, the instrument is adapted to be used by being inserted into the vertebral body through a working path formed in a vertebra, and the main body preferably has a scale for use in indicating a depth of insertion, the scale extending in a longitudinal direction of the main body along the peripheral surface thereof. Provision of this scale enables a position of the distal end of the impacting section within the vertebral body to be readily determined.

Yet another aspect of the invention is directed to a set of surgical instruments for use in the treatment of vertebral body compression fractures, the set comprising at least one instrument for reducing deformity having any one of features described above. With this set of surgical instruments, it is possible to treat collapsed vertebral bodies easily and reliably.

In this case, said at least one instrument preferably includes two or more different type instruments for reducing deformity for selective use depending on a region to be reduced in the vertebral body, which makes it possible to treat collapsed vertebral bodies more reliably.

Preferably, the set further includes at least one instrument for widening a working path having any one of features described above, which makes it possible to treat collapsed vertebral bodies more easily and reliably.

In this case, said at least one instrument preferably includes two or more instruments for widening a working path, in which each rod-shaped body has a different outer diameter. This makes it possible to increase the diameter of a working path formed in at least a vertebral body in multiple steps.

Also preferably, the set further includes the instrument for inserting a filler having any one of features described above, and the instrument for impacting the inserted filler having any one of features described above. With this set, it is possible to treat collapsed vertebral bodies more easily and reliably.

Moreover, each of the instruments in the set preferably has a different grip section, which difference enables the instruments to be readily distinguished.

Moreover, each of the instruments can be identified by its grip section. This makes it possible to easily identify the kind of the instrument, and therefore prevent accidental use of an inappropriate instrument.

DETAILED DESCRIPTION OF THE INVENTION

Hereinbelow, preferred embodiments of an instrument for widening a working path, an instrument for reducing deformity, an instrument for inserting a filler, an instrument for impacting the inserted filler, and a set of surgical instruments comprised of these instruments according to the present invention will be described in detail with reference to the accompanying drawings.

Figure 1:
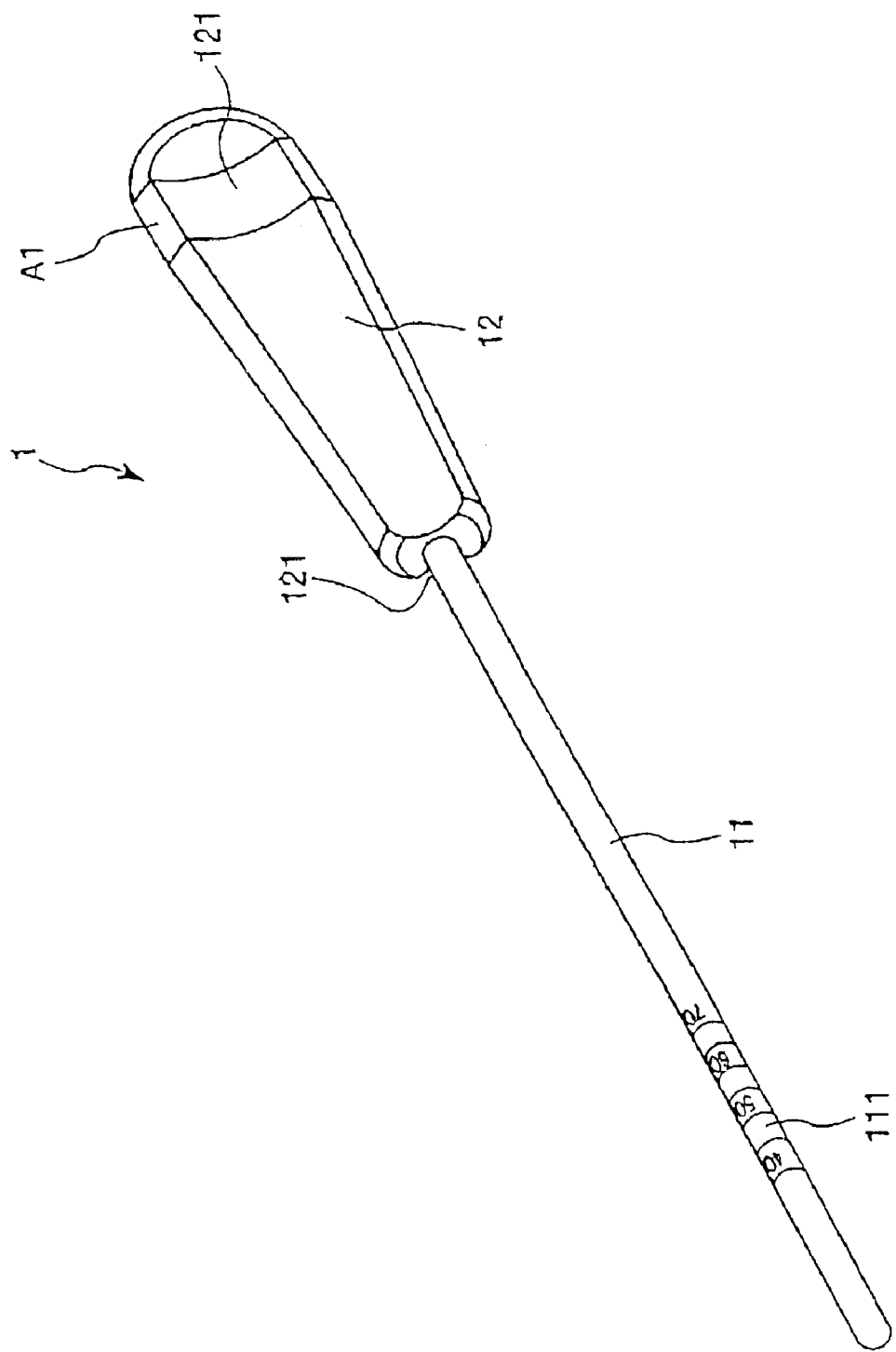
FIG. 1 is a perspective view which shows the structure of an instrument for widening a working path according to the present invention.
Figure 2:
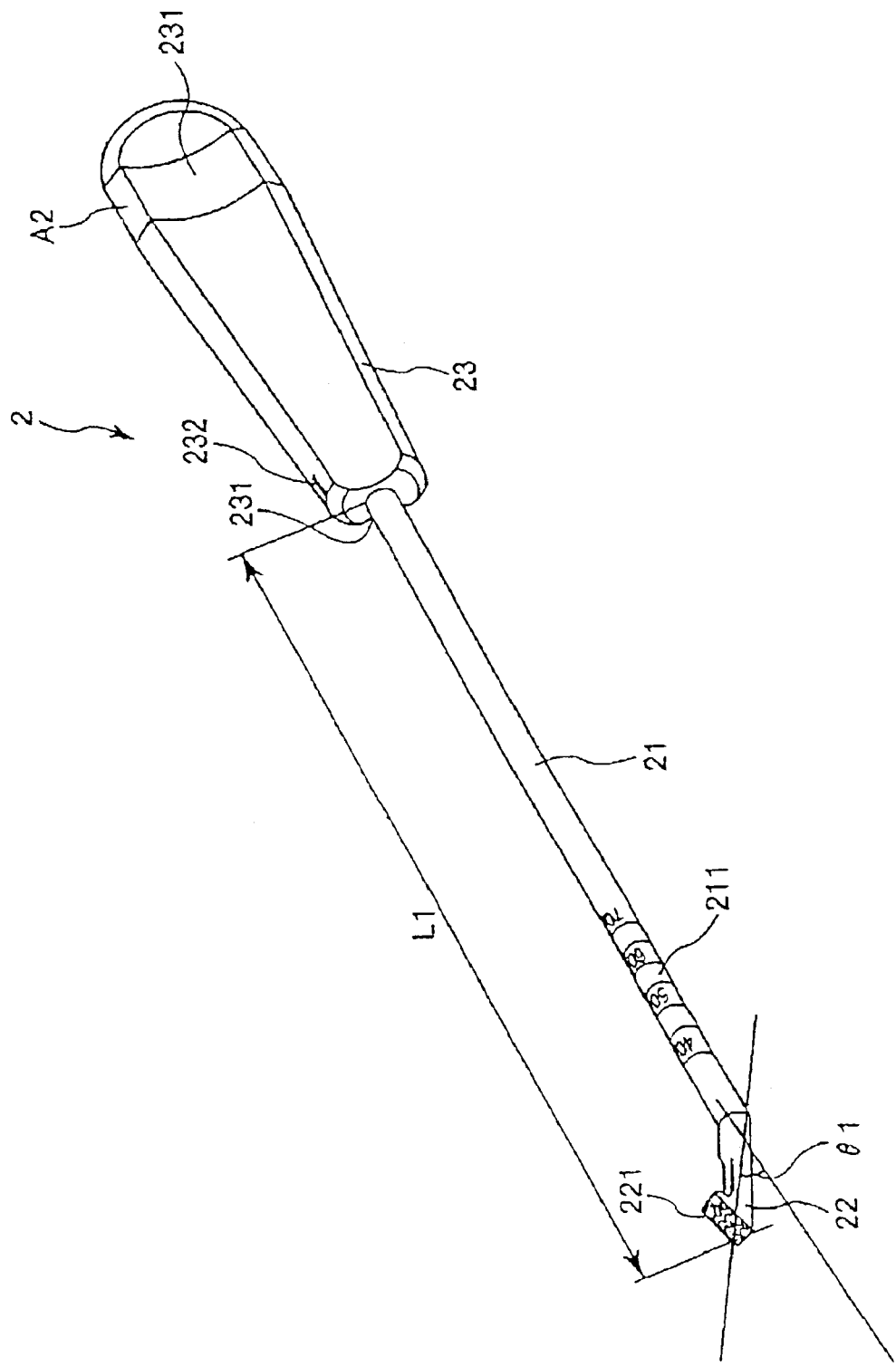
FIG. 2 is a perspective view which shows the structure of an instrument for reducing deformity according to the present invention.
Figure 3:
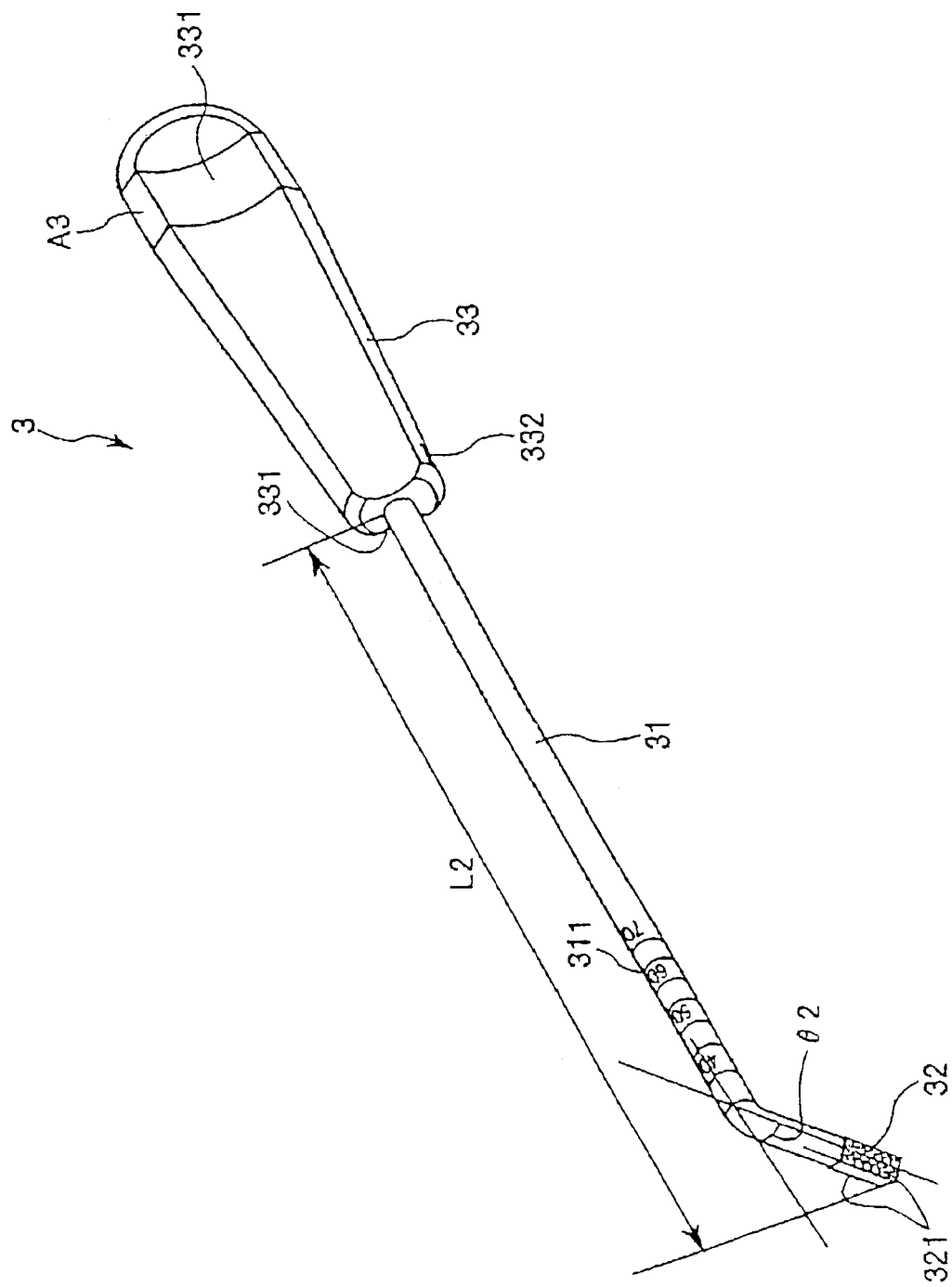
FIG. 3 is a perspective view which shows the structure of another instrument for reducing deformity according to the present invention.
Figure 4:
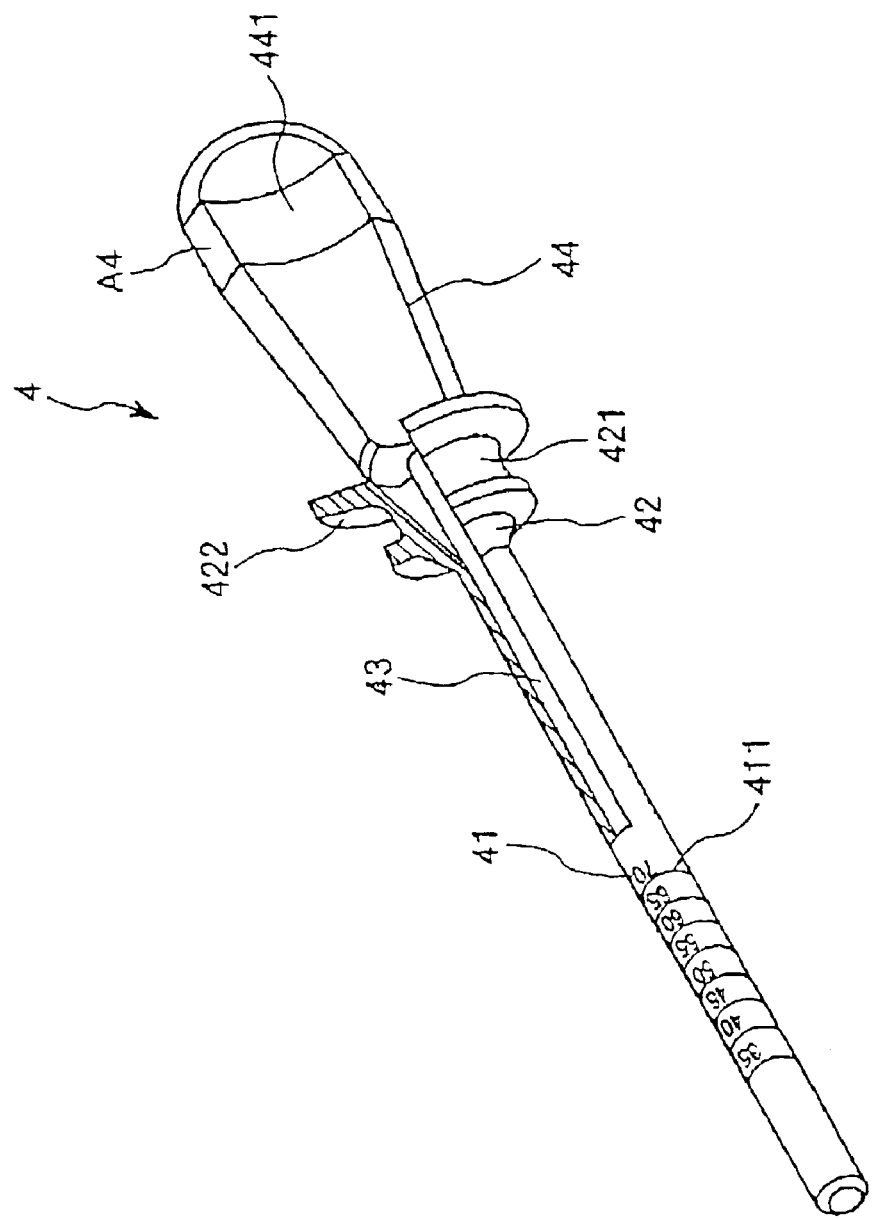
FIG. 4 is a perspective view which shows the structure of an instrument for inserting a filler according to the present invention.
Figure 5:
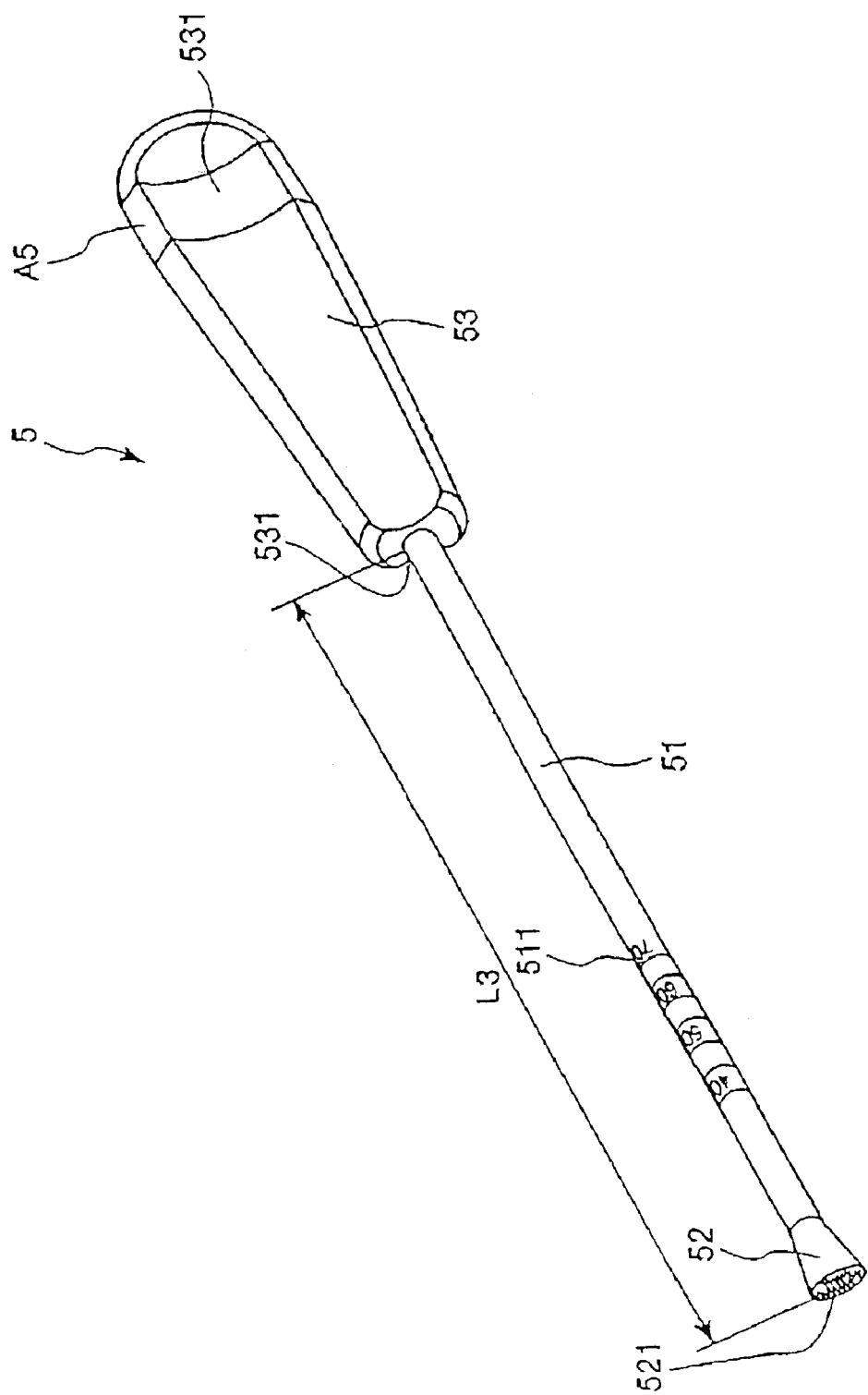
FIG. 5 is a perspective view which shows the structure of an instrument for impacting a filler according to the present invention.
Figure 6:
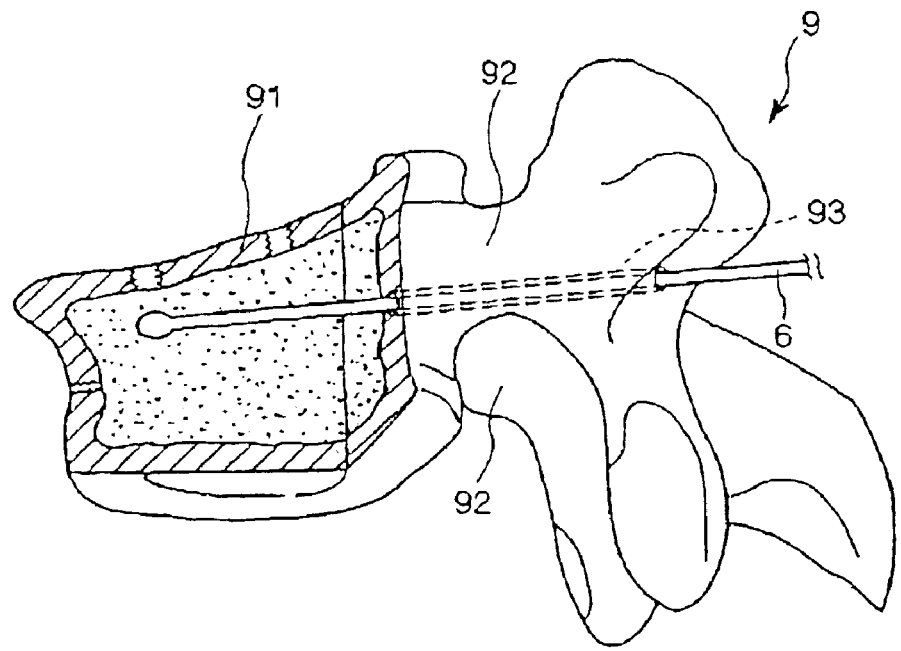
FIGS. 6(A) and (B) are schematic views of a vertebra for explaining the use of a set of surgical instruments according to the present invention.
Figure 6:
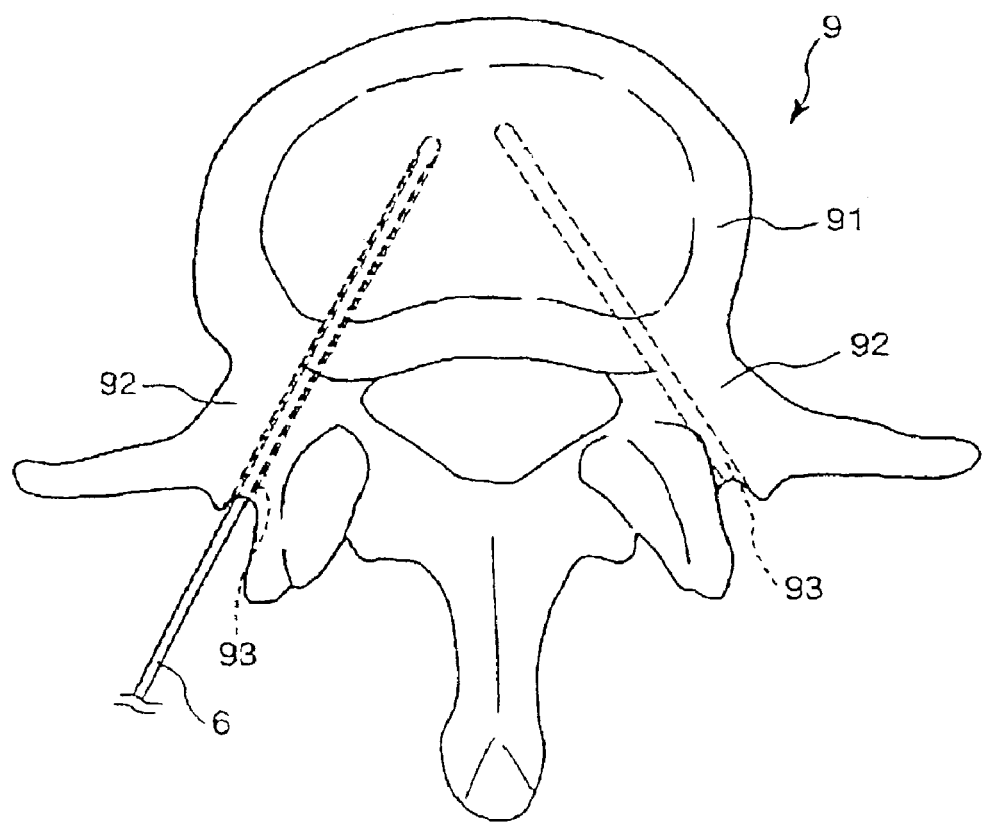

FIG. 1 is a perspective view which shows the structure of the instrument for widening a working path according to the present invention; FIG. 2 is a perspective view which shows the structure of the instrument for reducing deformity according to the present invention; FIG. 3 is a perspective view which shows the structure of another instrument for reducing deformity according to the present invention; FIG. 4 is a perspective view which shows the structure of the instrument for inserting a filler according to the present invention; FIG. 5 is a perspective view which shows the structure of the instrument for impacting a filler according to the present invention; FIGS. 6 to 11 are schematic views of a vertebra for explaining the use of the set of surgical instruments according to the present invention; and FIG. 12 is a schematic view of a vertebra in which a vertebral body that has collapsed as a result of a compression fracture has been treated. It is to be noted that FIGS. 6(A), 7(A), 8(A), 9(A), 10(A), and 11(A) are perspective views of a vertebra in which a vertebral body is partially cut away, as viewed from the bottom, and FIGS. 6(B), 7(B), 8(B), 9(B), 10(B), and 11(B) are plan views of the vertebra. Hereinafter, in relation to FIGS. 1 to 5, the left side and the right side will be referred to as the "distal end" and the "proximal ends", respectively. Also, in relation to FIGS. 6(A), 7(A), 8(A), 9(A), 10(A), 11(A), and FIG. 12, the upper side and the lower side will be referred to as the "upper side (head side)" and the "lower side (leg side)", respectively; and the left side and the right side will be referred to as the "anterior side (ventral side)" and the "posterior side (dorsal side)", respectively.

The set of surgical instruments according to the present invention is used in the treatment of vertebral body compression fractures. The set includes: a guide rod 1 (the instrument for widening a working-path); a vertical elevator 2 (the instrument for reducing deformity); z horizontal elevator 3 (the instrument for reducing deformity); an inserter 4 (the instrument for inserting a filler); and an impactor 5 (the instrument for impacting a filler). Both the vertical elevator 2 and the horizontal elevator 3 are used for reducing deformity, and they are selectively used depending on a region to be reduced in a vertebral body 91. In the following description, each of the surgical instruments (components) in the above will be described in order., <Guide Rod>

Figure 7:
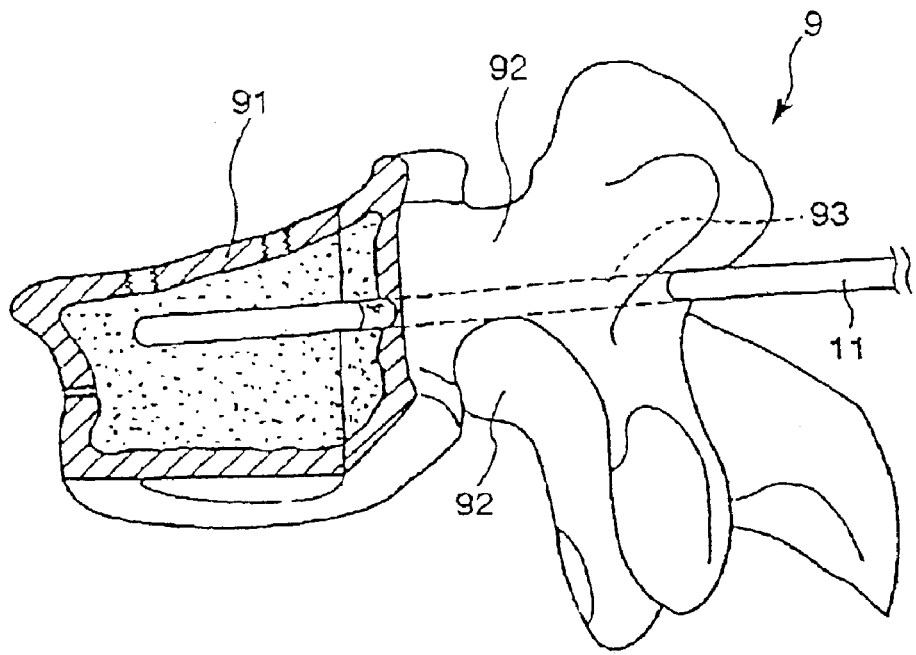
FIGS. 7(A) and (B) are schematic views of a vertebra for explaining the use of the set of surgical instruments according to the present invention.
Figure 7:
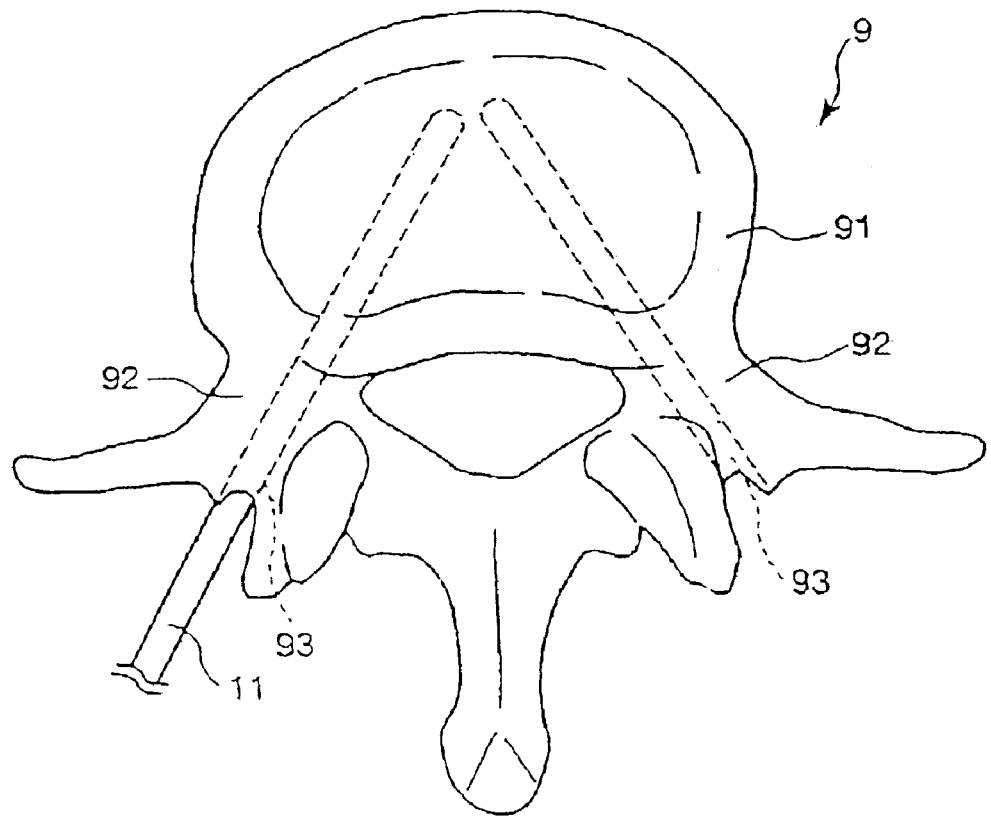

The guide rod 1 shown in FIG. 1 and FIG. 7 is a surgical instrument used for widening a path 93 formed in a vertebra 9 having a collapsed vertebral body 91. In general, the path 93 is formed so as to pass through a vertebral arch 92 into the inside of the vertebral body 91. In this regard, it is to be noted that the path 93 is formed on each side of the vertebral arch 92, that is, two paths 93, 93 are formed in the vertebra 9.

The guide rod 1 is constructed from a rod-shaped body 11 and a grip section 12. The rod-shaped body 11 has a substantially circular-shaped cross-section. The grip section 12 is provided on the proximal end of the rod-shaped body 11.

The guide rod 1 is adapted to be used by being inserted into the path 93 to widen the path 93.

Although variations exist between subjects for treatment, it is generally preferable that the internal diameter of the path 93 after the insertion of the rod-shaped body 11 into the path 93 is about 4.5 to 6.5 mm. By setting the internal diameter of the path 93 within the above range, it becomes possible to effectively perform operations (which will be described below) using the surgical instruments described above while preventing fracture of the vertebral arch 92, especially pedicles of the vertebral arch 92.

Further, it is preferable that the diameter of the path 93 is gradually increased in multiple steps. By gradually increasing the diameter of the path 93, a desired internal diameter of the path 93 can be obtained without the vertebral arch 92 being fractured, even in a case that a subject of the procedure is a patient having brittle bones as a result of, for example, osteoporosis.

In view of the foregoing, it is preferable that two or more guide rods 1 are prepared, in which each rod-shaped body 11 has a different outer diameter.

Furthermore, a length of the rod-shaped body 11 is not limited to any specific value, but it is preferably about 13 to 21 cm, and more preferably about 15 to 19 cm. By setting the length of the rod-shaped body 11 within the above range, handling of the guide rod 1 is made easier.

The distal end of the rod-shaped body 11 has a rounded form, by which it is possible to prevent adjacent tissue from being accidentally damaged during widening of the path 93.

The rod-shaped body 11 has a scale 111 for use in indicating a depth of insertion, and the scale 111 extends in a longitudinal direction of the rod-shaped body along the peripheral surface thereof. Therefore, even if the distal end portion of the rod-shaped body 11 is not visible while the guide rod 1 is being inserted in the path 93 formed in the vertebra 9, it is possible to readily determine a position of the distal end of the rod-shaped body 11 within the vertebral body 91.

Examples of the constituent material of the rod-shaped body 11 include various metal materials such as aluminum or an aluminum alloy, stainless steel, or titanium or a titanium alloy; various kinds of resin material such as polycarbonate, polymethyl methacrylate, polyimide, polysulfone, polyphenylene sulfide, polyetheretherketone, polyacetal, liquid crystal polymer, or polybutylene terephthalate; or various kinds of ceramic material such as alumina or hydroxy apatite. Among these materials, a metal material is preferable, and stainless steel is particularly preferable. By forming the rod-shaped body 11 using stainless steel, the rod-shaped body 11 is imparted with a high strength, a high impact resistance, and a sufficient heat resistance to withstand high temperatures during sterilization.

On the proximal end of the rod-shaped body 11, the grip section 12 is fixedly coupled by, for example, screwing, press fitting, caulking, welding or bonding, or by using screw. In operating the guide rod 1, the operator grips this grip section 12.

Further, the grip section 12 has two recesses 121, 121 provided in its longitudinal direction. These two recesses 121, 121 are provided opposite one another about an axis of the grip section 12, so as to enable the operator to firmly grip the grip section, and prevent the operator's hand from slipping.

<Vertical Elevator>

Figure 8:
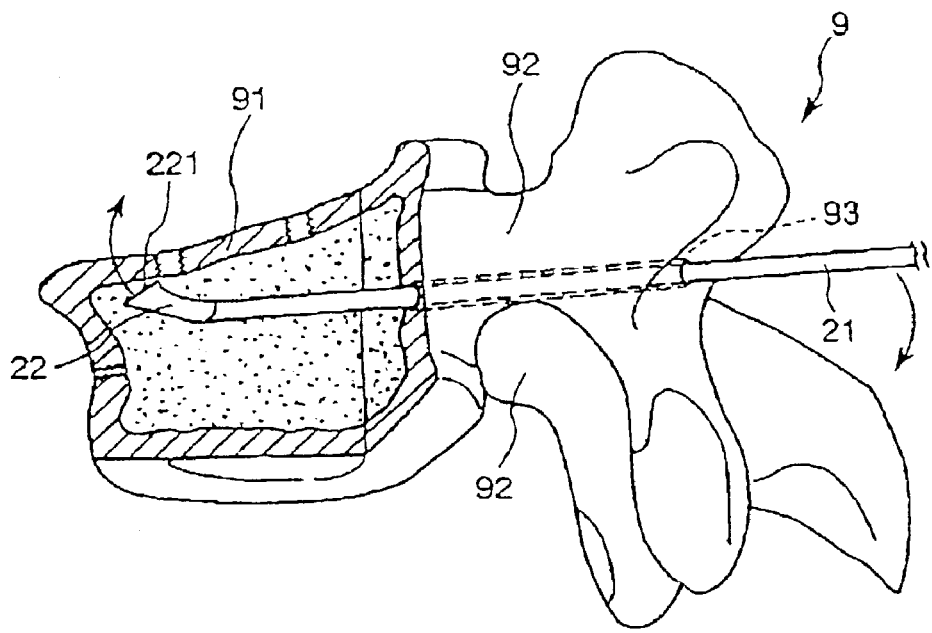
FIGS. 8(A) and (B) are schematic views of a vertebra for explaining the use of the set of surgical instruments according to the present invention.
Figure 8:
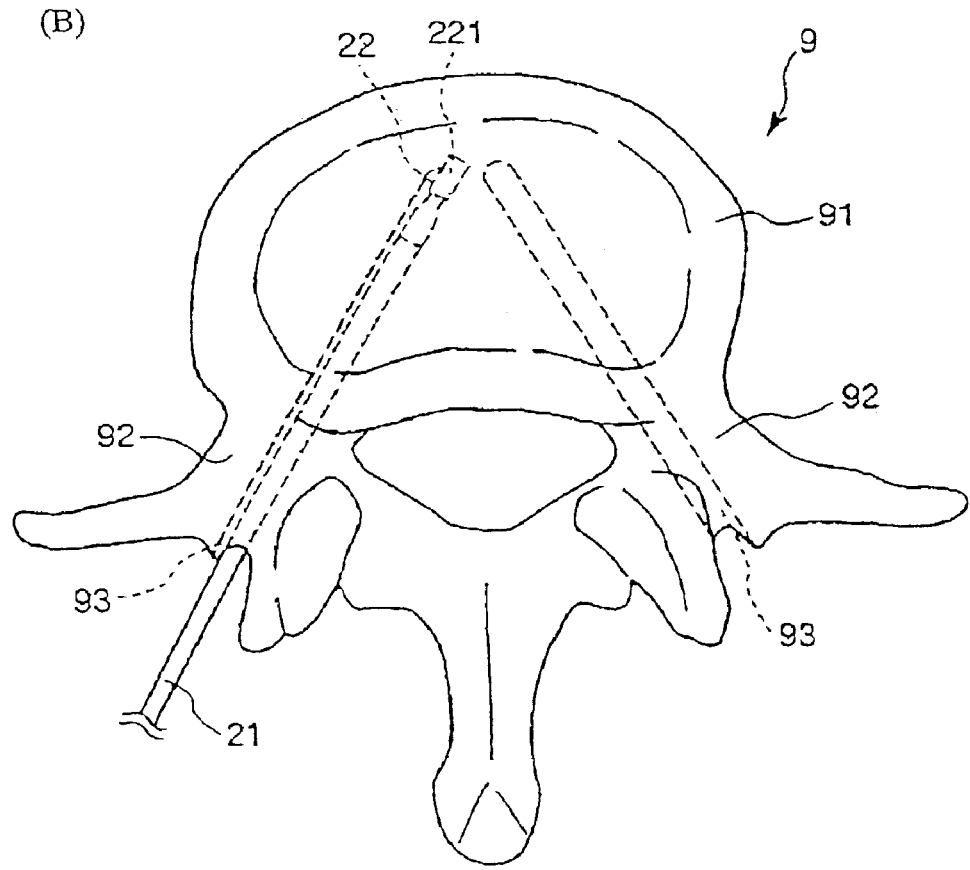

The vertical elevator 2 shown in FIG. 2 and FIG. 8 is a surgical instrument used for returning the upper portion, especially the upper anterior portion, of the vertebral body 91 to a substantially normal position.

The vertical elevator 2 is constructed from a rod-shaped main body 21, a pushing section 22 and a grip section 23. The pushing section 22 is provided on the distal end of the main body 21, and the grip section 23 is provided on the proximal end of the main body 21.

The main body 21 has a substantially circular-shaped cross section. Further, the main body 21 is formed such that the outer diameter is smaller than the internal diameter of the path 93 formed in the vertebra 9.

The vertical elevator 2 is adapted to be used by being inserted into the vertebral body 91 through the path 93 formed in the vertebra 9. The main body 21 has a scale 211 for use in indicating a depth of insertion, and the scale 211 extends in a longitudinal direction of the main body along the peripheral surface thereof. Therefore, even if the distal end portion of the vertical elevator 2 is not visible while the vertical elevator 2 is being inserted in the path 93 formed in the vertebra 9, it is possible to readily determine a position of the, distal end of the pushing section 22 (which will be described below) within the vertebral body 91.

On the distal end of the main body 21, the flat-shaped pushing section 22 is integrally formed with the main body 21, and the pushing section 22 is inclined to the main body 21.

The pushing section 22 is provided for pushing the upper portion of the vertebral body 91 in an upward direction.

In using the vertical elevator 2 having such a structure described above, the distal end portion of the vertical elevator 2 is inserted into the vertebral body 91 through the path 93 (see FIG. 8), and then the proximal end of the main body 21 is pushed in a downward direction so that a distal end surface 221 of the pushing section 22 comes into contact with the upper surface of the inside of the vertebral body 91, and so that the pushing section 22 pushes the upper anterior portion of the vertebral body 91. Consequently, the upper anterior portion of the vertebral body 91 is upwardly elevated.

That is, in the vertical elevator 2, the distal end surface 221 functions as a contact surface with the upper surface of the inside of the vertebral body 91.

The inclined angle between the pushing section 22 and the main body 21, which is indicated by θ1 in FIG. 2, is not limited to any specific value; but it is preferably about 5 to 30°, and more preferably about 5 to 15°. By setting the angle θ1 within the above range, it is possible to reduce the vertebral body 91 more easily and reliably while avoiding accidental fracture of pedicles of the vertebral arch 92.

The distal end surface 221 of the pushing section 22 is formed with irregularities. The surface irregularities makes it possible to prevent or to suppress slippage of the distal end surface 221 against the upper surface of the inside of the vertebral body 91. By using the vertical elevator 2 having the distal end surface 221 formed with irregularities, the vertebral body 91 can be more reliably reduced.

The shape of the surface irregularities is not particularly limited, but preferably projections of the irregularities have sharp edges, which makes it possible to prevent or to suppress slippage of the distal end surface 221 against the upper surface of the inside of the vertebral body 91 more reliably.

In this regard, it is to be noted that the projections may be arranged in a regular pattern such as a grid pattern or the like, or may be arranged in an irregular (random) pattern.

Further, the distal end surface 221 may be rough surface with very fine irregularities.

As for the constituent material of the pushing section 22 and the main body 21, materials which are the same as those used for the rod-shaped body 11 of the guide rod 1 described above may be employed.

The total length of the pushing section 22 and the main body 21, which is indicated by L1 in FIG. 2, is not limited to any specific value, but it is preferably about 13 to 21 cm, and more preferably about 15 to 19 cm. By setting the length within the above range, handling of the vertical elevator 2 is made easier.

It is to be noted that the vertical elevator 2 is not limited to one in which the pushing section 22 and the main body 21 are integrally formed. In the vertical elevator 2, the pushing section 22 may be fixedly mounted to the main body 21 by, for example, screwing or fitting them together.

Further, on the proximal end of the main body 21, the grip section 23 is fixedly coupled by, for example, screwing, press fitting, caulking, welding or bonding, or by using screw. In operating the vertical elevator 2, the operator grips this grip section 23.

The grip section 23 has two recesses 231, 231 provided in its longitudinal direction. These two recesses 231, 231 are provided opposite one another about an axis of the grip section 23, so as to enable the operator to firmly grip the grip section, and prevent the operator's hand from slipping.

The vertical elevator 2 has a marker 232 which indicates a direction in which the pushing section 22 is inclined, that is, a direction in which the pushing section 22 points. The marker 232 is provided on the peripheral surface of the grip section 23 such that the position of the marker corresponds to a direction in which the distal end surface 221 points. The marker may be formed from a specific color indicated on the peripheral surface. (In FIG. 2, the marker 232 is provided on the upper side.) By providing the marker, even if the distal end portion of the vertical elevator 2 is not visible while the vertical elevator 2 is being inserted in the path 93 formed in the vertebra 9, it is possible to readily determine a direction in which the pushing section 22, especially the distal end surface 221 points within the vertebral body 91.

In this regard, it is to be noted that while the marker 232 of the present embodiment is provided on the grip section 23, it may be provided on a part other than the grip section 23, for example, on the proximal end portion of the main body 21.

<Horizontal Elevator>

Figure 9:
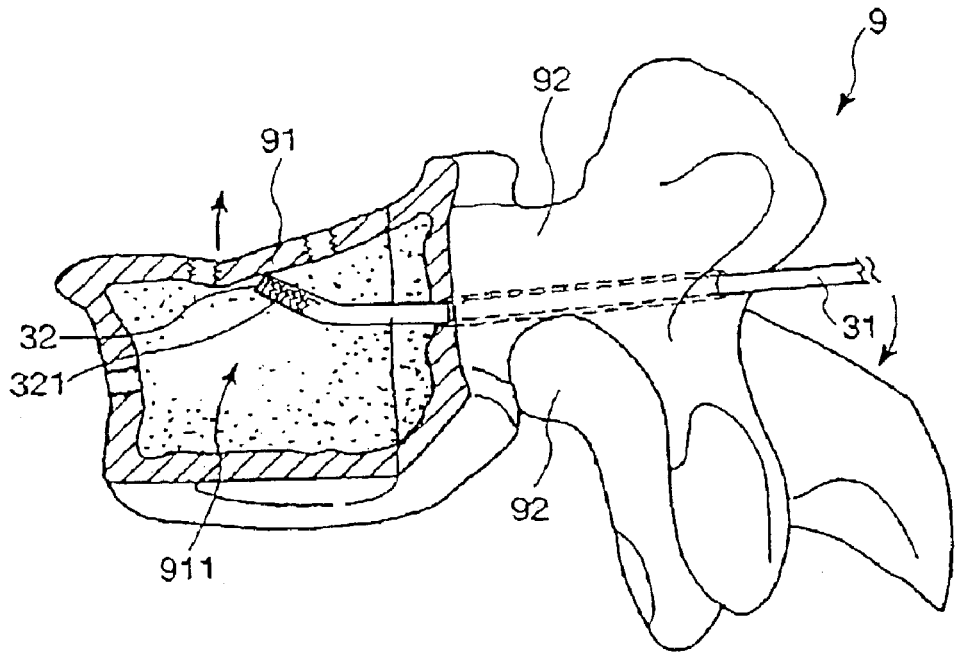
FIGS. 9(A) and (B) are schematic views of a vertebra for explaining the use of the set of surgical instruments according to the present invention.
Figure 9:
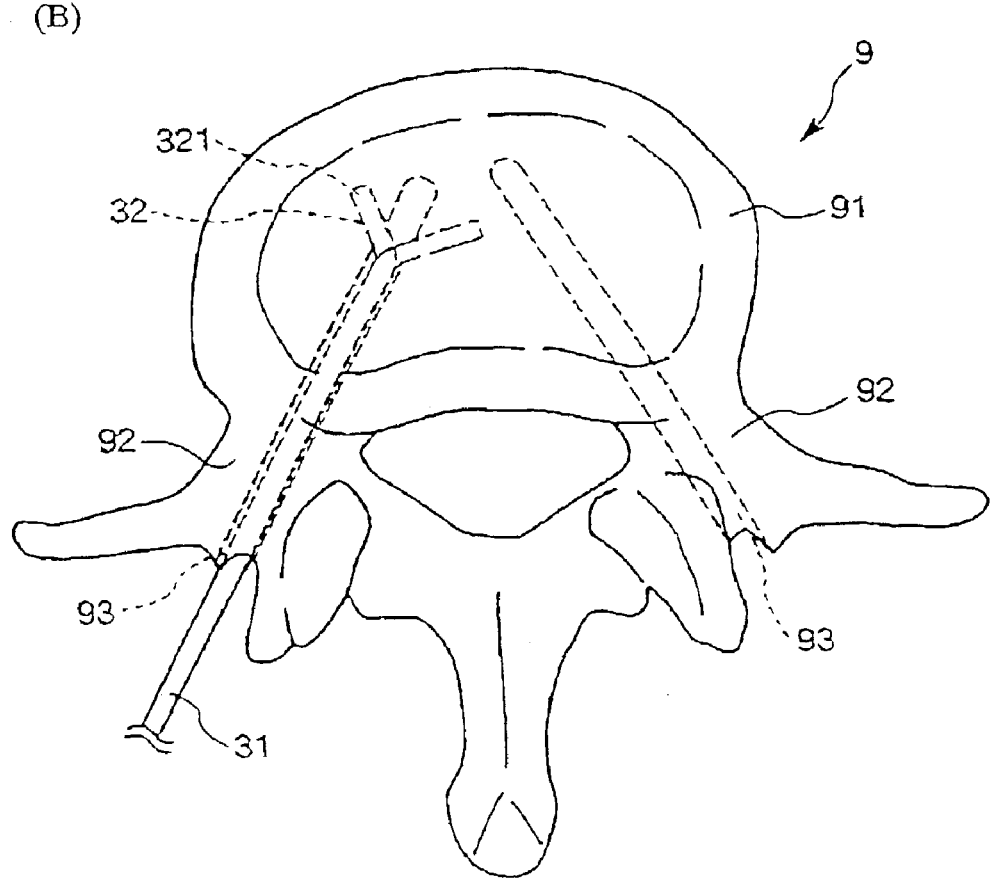

The horizontal elevator 3 shown in FIG. 3 and FIG. 9 is a surgical instrument used for returning the upper portion, especially the upper middle portion, of the vertebral body 91 to a substantially normal position.

The horizontal elevator 3 is constructed from a rod-shaped main body 31, a pushing section 32, and a grip section 33. The pushing section 32 is provided on the distal end of the main body 31, and the grip section 33 is provided on the proximal end of the main body 31.

The main body 31 has a substantially circular-shaped cross section. Further, the main body 31 is formed such that the outer diameter is smaller than the internal diameter of the path 93 formed in the vertebra 9.

The horizontal is adapted to be used by being inserted into the vertebral body 91 through the path 93 formed in the vertebra 9. The main body 31 has a scale 311 for use in indicating a depth of insertion, and the scale 311 extends-in a longitudinal direction of the main body 31 along the peripheral surface thereof. Therefore, even if the distal end portion of the horizontal elevator 3 is not visible while the horizontal elevator 3 is being inserted in the path 93 formed in the vertebra 9, it is possible to readily determine a position of the distal end of the pushing section 32 (which will be described below) within the vertebral body 91.

On the distal end of the main body 31, the flat-shaped pushing section 32 is integrally formed. The pushing section 32 is provided for pushing the upper portion of the vertebral body 91 in an upward direction.

In using the horizontal elevator 3 having the structure described above, the distal end portion of the horizontal elevator 3 is inserted into the vertebral body 91 through the path 93 (see FIG. 9), and then the proximal end of the main body 31 is pushed in a downward direction so that one of side surfaces 321 of the pushing section 32 comes into contact with the upper surface of the inside of the vertebral body 91, and so that the pushing section 32 pushes the upper middle portion of the vertebral body 91. Consequently, the upper middle portion of the vertebral body 91 is upwardly elevated.

In the present embodiment, each of the pair of side surfaces 321, 321 (which are positioned on the front and back sides in FIG. 3) functions as the contact surface described above. However, in the horizontal elevator 3, at least a part of the peripheral surface of the pushing section 32 may function as the contact surface which comes into contact with the upper surface of the inside of the vertebral body 91.

Each of the side surfaces 321, 321 of the pushing section 32 has irregularities. The surface irregularities makes it possible to prevent or to suppress slippage of the side surface 321 against the upper surface of the inside of the vertebral body 91. By using the horizontal elevator 3 having the side surfaces 321, 321 formed with irregularities, the vertebral body 91 can be more reliably reduced.

The shape of the surface irregularities is not particularly limited, but it is preferable that projections of the irregularities have sharp edges, which makes it possible to more reliably prevent or to suppress slippage of the side surface 321 against the upper surface of the inside of the vertebral body 91.

In this regard, it is to be noted that the projections may be arranged in a regular pattern such as a grid pattern or the like, or may be arranged in an irregular (random) pattern.

Further, each side surface 321 may be rough surface with very fine irregularities.

The pushing section 32 is inclined to the main body 31. Therefore, by turning the pushing section 32 about an axis of the main body 31 (see FIG. 9(B)), it is possible to perform the reduction procedure on the vertebral body 91 over a wide range.

The inclined angle between the pushing section 32 and the main body 31, which is indicated by θ2 in FIG. 3, is not limited to any specific value, but it is preferably about 5 to 30°, and more preferably about 5 to 15°. By setting the angle θ2 within the above range, it is possible to reduce the vertebral body 91 over a wider range.

As for the constituent material of the pushing section 32 and the main body 31, materials which are the same as those used for the rod-shaped body 11 of the guide rod 1 described above may be employed.

The total length of the pushing section 32 and the main body 31 (which is indicated by L2 in FIG. 3) is not limited to any specific value, but it is preferably about 13 to 21 cm, and more preferably about 15 to 19 cm. By setting the length within the above range, handling of the horizontal elevator 3 is made easier.

It is to be noted that the horizontal elevator 3 is not limited to one in which the pushing section 32 and the main body 31 are integrally formed. In the horizontal elevator 3, the pushing section 32 may be fixedly mounted to the main body 31 by, for example, screwing or fitting them together.

On the proximal end of the main body 31, the grip section 33 is fixedly coupled by, for example, screwing, press fitting, caulking, welding or bonding, or by using screw. In operating the horizontal elevator 3, the operator grips this grip section 33.

Further, the grip section 33 has two recesses 331, 331 provided in its longitudinal direction. These two recesses 331, 331 are provided opposite one another about an axis of the grip section 33 so as to enable the operator to firmly grip the grip section, and prevent the operator's hand from slipping.

The horizontal elevator 3 has a marker 332 which indicates a direction in which the pushing section 32 is inclined, that is, a direction in which the pushing section 32 points. The marker 332 is provided by, for example, a color, on the peripheral surface of the grip section 33 so as to form a substantially right angle with the side surfaces 321, 321 (in FIG. 3, the marker 332 is provided on the lower side). By providing such a marker, even if the distal end portion of the horizontal elevator 3 is not visible while the horizontal elevator 3 is being inserted in the path 93 formed in the vertebra 9, it is possible to readily determine a direction in which the pushing section 32 points within the vertebral body 91. In this case, the operator can determine that the side surfaces 321, 321 point in a direction that is at a substantially right angle to the marker 332.

In this regard, it is to be noted that while the marker 332 of the present embodiment is provided on the grip section 33, it may be provided on a part other than the grip section 33, for example, on the proximal end portion of the main body <Inserter>

Figure 10:
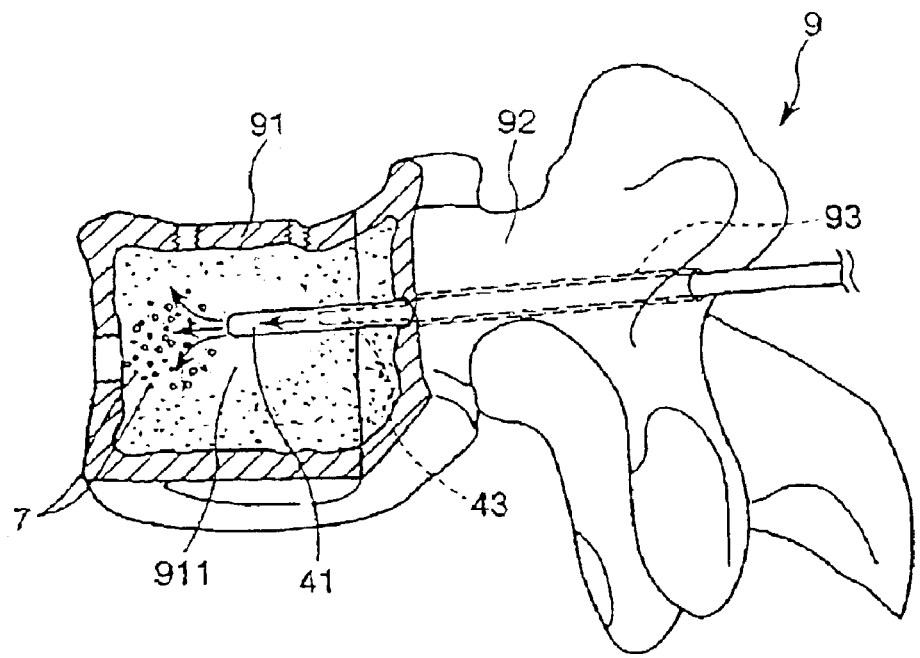
FIGS. 10(A) and (B) are schematic views of a vertebra for explaining the use of the set of surgical instruments according to the present invention.
Figure 10:
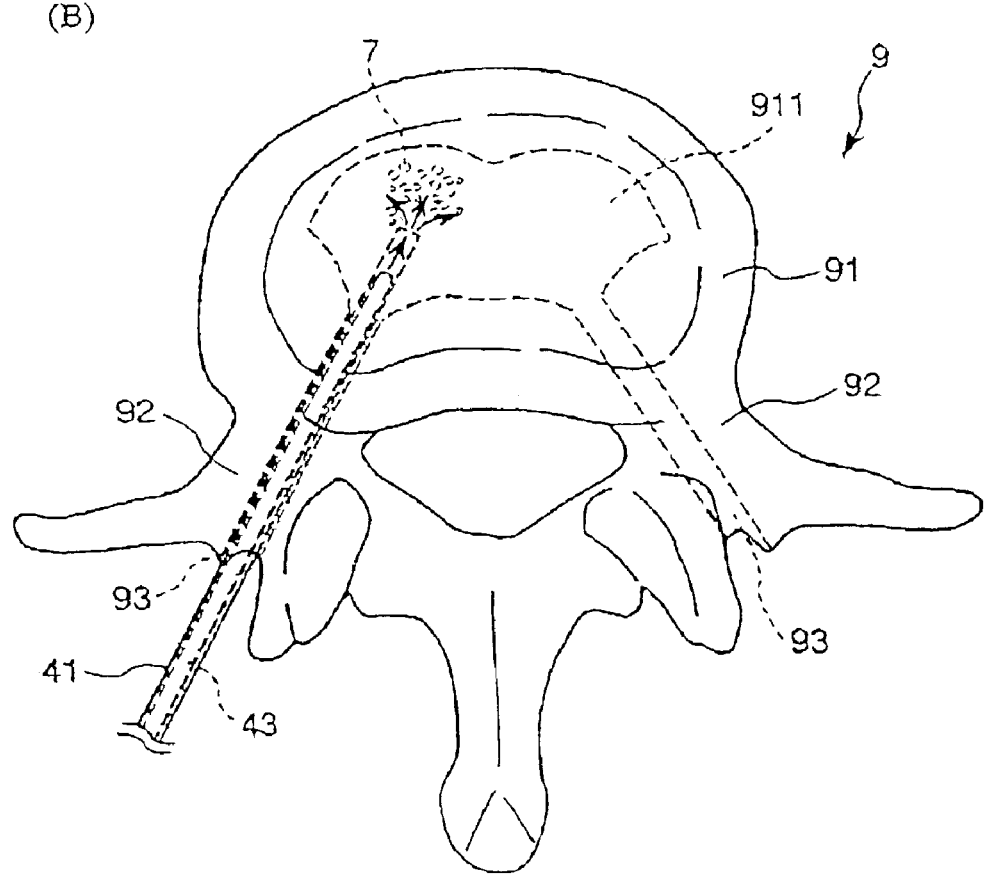

The inserter 4 shown in FIG. 4 and FIG. 10 is a surgical instrument used for inserting a filler 7 into the inside of the reduced vertebral body 91 (that is a cavity 911 created within the vertebral body 91 after the reduction procedure described above).

The inserter 4 is constructed from a tubular body 41, an ejector bar 43, a tubular body grip section 42, and an ejector bar grip section 44. The tubular body grip section 42 is provided on the proximal end of the tubular body 41, and the ejector bar grip section 44 is provided on the proximal end of the ejector bar 43.

The tubular body 41 is formed from a cylindrical member with both ends open. Specifically, the tubular body 41 has a lumen passing through from the proximal end to the distal end thereof, into which the ejector bar 43 is to be inserted. The lumen is filled with the filler 7 (which will be described below).

The tubular body 41 is formed such that the outer diameter has substantially the same diameter as the internal diameter of the path 93 formed in the vertebra 9. This makes it possible to prevent the filler 7 from leaking out of the vertebra 9 from the space between the outer surface of the tubular body 41 and the internal surface of the path 93 during insertion of the filler 7 into the vertebral body 91.

The length of the tubular body 41 is not limited to any specific value, but it is preferably about 9 to 17 cm, and more preferably about 11 to 15 cm. By setting the length of the tubular body 41 within the above range, handling of the inserter 4 is made easier.

The tubular body 41 of the inserter 4 is adapted to be used by being inserted into the vertebral body 91 through the path 93 formed in the vertebra 9. The tubular body 41 has a scale 411 for use in indicating a depth of insertion, and the scale 411 extends in a longitudinal direction of the tubular body along the peripheral surface thereof. Therefore, even if the distal end portion of the inserter 4 is not visible while the inserter 4 is being inserted in the path 93 formed in the vertebra 9, it is possible to readily determine a position of the distal end of the tubular body 41 or a position of the distal end of the ejector bar 43 (which will be described below) within the vertebral body 91.

As for the constituent material of the tubular body 41 and the ejector bar 43, materials which are the same as those used for the rod-shaped body 11 of the guide rod 1 described above may be employed. In this regard, it is to be noted that both the tubular body 41 and the ejector bar 43 are preferably formed of stainless steel. By forming the tubular body 41 and the ejector bar 43 using stainless steel, a sliding property between the internal surface of the tubular body 41 and the external surface of the ejector bar 43 becomes excellent (that is, friction between the surfaces is reduced), while they are imparted with a high shock resistance and an excellent heat resistance, as described above, so that it becomes easier to slide the ejector bar 43 within the tubular body 41.

On the proximal end of the tubular body 41, the tubular body grip section 42 is fixedly coupled by, for example, screwing, press fitting, caulking, welding or bonding, or by using screw. In operating the inserter 4, the operator grips this tubular body grip section 42.

The tubular body grip section 42 is formed from a substantially cylindrical member. In the longitudinal middle portion of the tubular body grip section 42, a recess 421 is formed in a circumferential direction. Further, the tubular body grip section 42 has an annular flange 422 provided on its proximal end. Both the recess 421 and the annular flange 422 are provided to prevent the operator's hand from slipping. By forming the recess 421 and flange 422 in the tubular body grip section 42, the operator is able to firmly grip the tubular body grip section 42, and therefore reliably operate the inserter 4.

The internal diameter of the tubular body grip section 42 is gradually increased toward its proximal end. By gradually increasing the internal diameter, it is possible to more easily and reliably feed the filler 7 into the lumen of the tubular body 41 and insert the ejector bar 43 into the lumen of the tubular body 41. The filler 7 filled in the lumen of the tubular body 41 is ejected by inserting the ejector bar 43 into the lumen.

The ejector bar 43 has a substantially circular-shaped cross section. Further, the ejector bar 43 is formed such that the outer diameter has substantially the same diameter as the internal diameter of the tubular body 41. The outer diameter of the ejector bar 43, that is, the internal diameter of the tubular body 41 is not limited to any specific value, but it is preferably about 3 to 6 mm.

Furthermore, the distal end of the ejector bar 43 has a rounded form. Such a rounded distal end of the ejector bar 43 prevents adjacent tissue from being accidentally damaged during insertion of the filler 7.

The ejector bar 43 is formed such that the distal end thereof projects outward from the distal end of the tubular body 41 when the ejector bar 43 is fully inserted in the tubular body 41, that is, when the distal end of the ejector bar grip section 44 abuts the proximal end of the tubular body grip section 42. Namely, the length of the ejector bar 43 is set such that the distal end thereof projects outward from the tubular body 41 when the ejector bar 43 is fully inserted in the tubular body 41. By using the ejector bar 43 having such a structure, it is possible to effectively eject the filler 7 from the lumen of the tubular body 41.

In this regard, it is to be noted that the ejector bar, 43 need not necessarily be a solid type, and may be a hollow type. As for the hollow type ejector bar 43, one in which at least one of the both ends is closed or one in which both the ends are open may be employed. In the latter case, for example, a sheath (tubular body), a catheter tube and the like can be mentioned.

On the proximal end of the ejector bar 43, the ejector bar grip section 44 is fixedly coupled by, for example, screwing, press fitting, caulking, welding or bonding, or by using screw. In operating the inserter 4, the operator grips this ejector bar grip section 44.

Further, the ejector bar grip section 44 has two recesses 441, 441 along its longitudinal direction. These two recesses 441, 441 are provided opposite one another about an axis of the ejector bar grip section 44, to enable the operator to firmly grip the grip section, and to prevent the operator's hand from slipping.

As for the filler 7 used for the present invention, powder materials used as a bone prosthesis (biomaterial) are preferable. In this regard, it is to be noted that the term "powder" used in this specification has a broad meaning that includes powder particles, granules, fine flakes, fine needles, and the like. Also, the shape, form, and manufacturing method thereof are not particularly limited.

Examples of materials used for the powder materials include various kinds of ceramics such as alumina, zirconia, calcium phosphate-based compounds, and the like. Among these materials, calcium phosphate-based compounds are preferable. This is because, since a calcium phosphate-based compound remains stable in a living body over a long period of time, it is particularly suitable for use as a biomaterial.

Examples of the calcium phosphate-based compounds include hydroxy apatite ($Ca_{10}(PO_4))_6(OH)_2$), TCP ($Ca_3(PO_4)_2$), $Ca_2P_2O_7$, $Ca(PO_3)_2$, $Ca_{10}(PO_4)_6F_2$, $Ca_{10}(PO_4)_6Cl_2$, $DCPD(CaHPO_4 \cdot 2H_2O)$, $Ca_4O(PO_4)_2$, and the like, and one kind of or a mixture of two or more kinds of these calcium phosphate-based compounds may be employed.

The average particle size of powders is not limited to a specific value, but it is preferably about 0.1 to 6.0 mm, and more preferably about 1.0 to 5.0 mm.

<Impactor>

Figure 11:
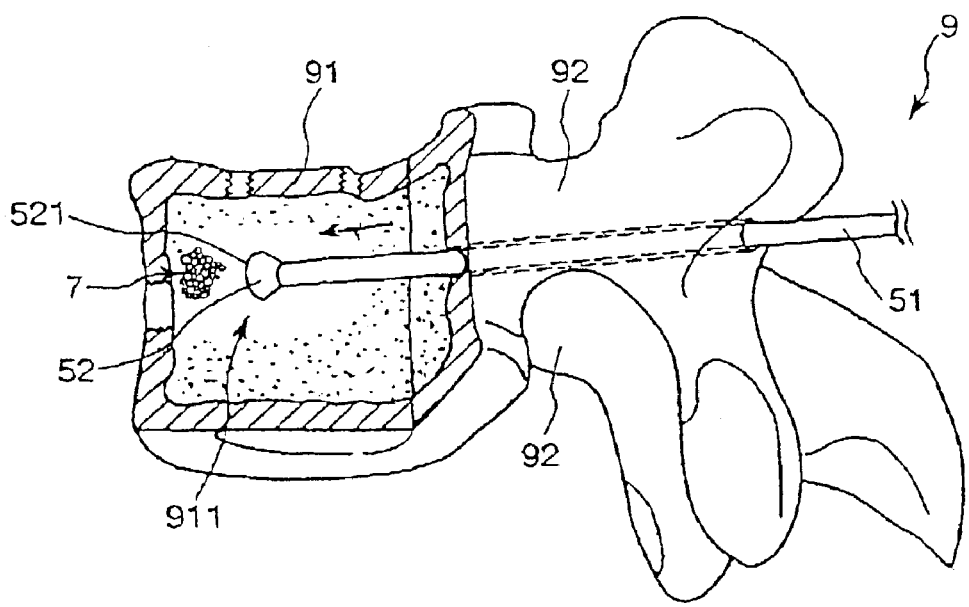
FIGS. 11(A) and (B) are schematic views of a vertebra for explaining the use of the set of surgical instruments according to the present invention.
Figure 11:
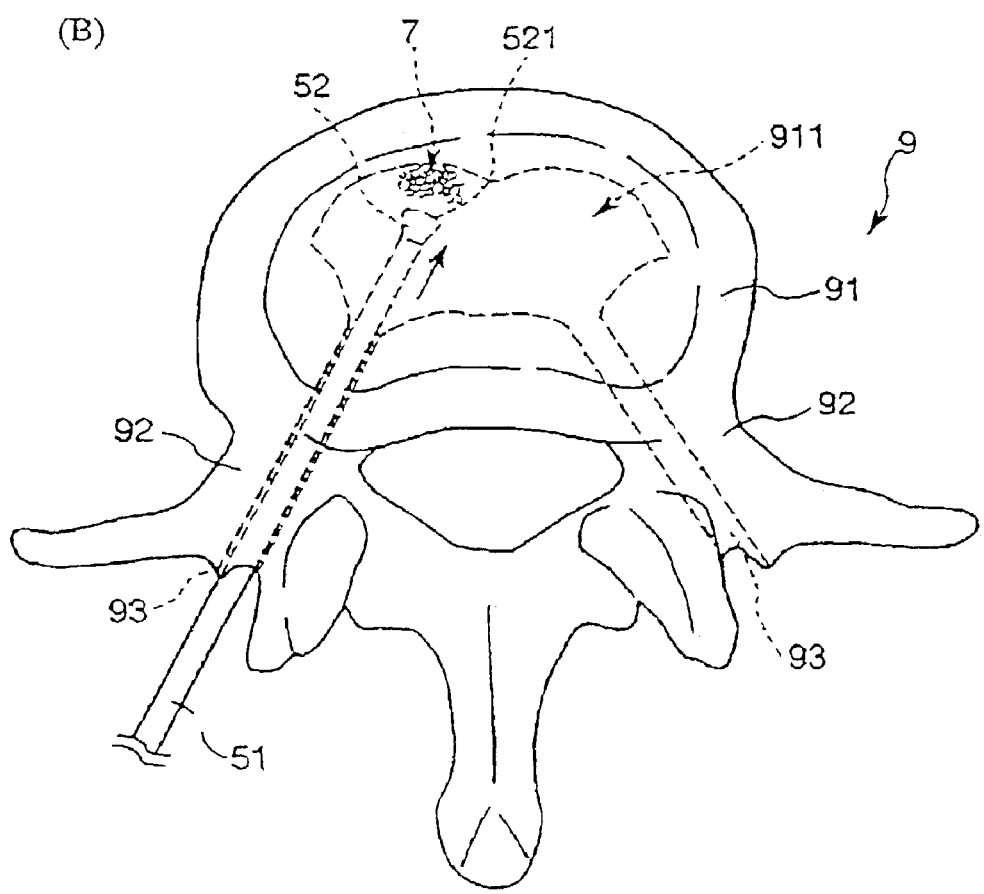
Figure 12:
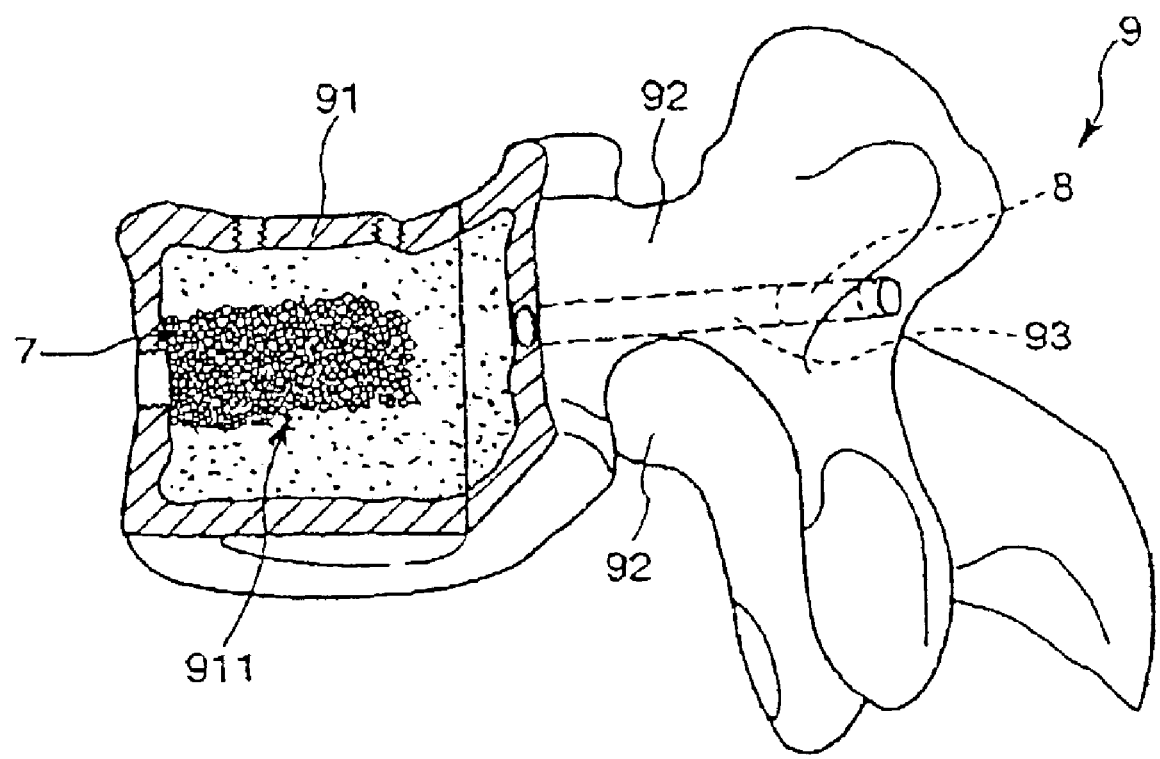
FIG. 12 is a schematic view of a vertebra in which a vertebral body that has collapsed as a result of a compression fracture has been treated.

The impactor 5 shown in FIG. 5 and FIG. 11 is a surgical instrument used for impacting the filler 7 inserted in the reduced vertebral body 91 to a high density.

The impactor 5 is constructed from a rod-shaped main body 51, an impacting section 52, and a grip section 53. The impacting section 52 is provided on the distal end of the main body 51, and the grip section 53 is provided on the proximal end of the main body 51.

The main body 51 has a substantially circular-shaped cross section. Further, the main body 51 is formed such that the outer diameter is smaller than the internal diameter of the path 93 formed in the vertebra 9.

The impactor 5 is adapted to be used by being inserted into the vertebral body 91 through the path 93 formed in the vertebra 9. The main body 51 has a scale 511 for use in indicating a depth of insertion, and the scale 511 extends in a longitudinal direction of the main body 51 along the peripheral surface thereof. Therefore, even if the distal end portion of the impactor 5 is not visible while the impactor 5 is being inserted in the path 93 formed in the vertebra 9, it is possible to readily determine a position of the distal end of the impacting section 52 within the vertebral body 91.

On the distal end of the main body 51, the impacting section 52 is integrally formed. The impacting section 52 has a substantially cylindrical shape.

The impacting section 52 has a distal end surface 521 which impacts the filler 7 within the vertebral body 91. When using the impactor 5 having the distal end surface 521, the impactor is pushed toward the anterior portion (which is on the left side in FIG. 11(A)) so that the distal end surface 521 impacts the filler 7, thereby enabling the filler 7 to be compacted to a high density (filling density).

The distal end surface 521 has irregularities. The surface irregularities allows the distal end surface 521 to catch the filler 7, especially the powder type of filler 7. Therefore, it is possible to effectively compact the filler to a high density by using such an impactor 5.

The shape of the surface irregularities is not particularly limited, but it is preferable that projections of the irregularities have sharp edges. Such projections allow the distal end surface 521 to catch the filler 7 more effectively.

In this regard, it is to be noted that the projections may be arranged in a regular pattern such as a grid pattern or the like, or may be arranged in an irregular (random) pattern.

Further, the distal end surface 521 may be rough surface with very fine irregularities.

The outer diameter of the impacting section 52 is gradually increased toward its distal end. This increases an area of contact between the impacting section 52 and the filler 7, thereby enabling the filler 7 to be compacted more effectively.

In this regard, it is to be noted that the impacting section 52 is formed such that the outer diameter of the distal end has substantially the same diameter as the internal diameter of the path 93 formed in the vertebra 9.

As for the constituent material of the impacting section 52 and the main body 51, materials which are the same as those used for the rod-shaped body 11 of the guide rod 1 described above may be employed.

The total length of the impacting section 52 and the main body 51 (which is indicated by L3 in FIG. 5) is not limited to any specific value, but it is preferably about 13 to 21 cm, and more preferably about 15 to 19 cm. By setting the length within the above range, handling of the impactor 5 is made easier.

It is to be noted that the impactor 5 is not limited to one in which the impacting section 52 and the main body 51 are integrally formed. In the impactor 5, the impacting section 52 may be fixedly mounted to the main body 51 by, for example, screwing or fitting them together.

On the proximal end of the main body 51, the grip section 53 is fixedly coupled by, for example, screwing, press fitting, caulking, welding or bonding, or by using screw. In operating the impactor 5, the operator grips this grip section 53.

Further, the grip section 53 has two recesses 531, 531 provided in its longitudinal direction. These two recesses 531, 531 are provided opposite one another about an axis of the grip section 53 to enable the operator to firmly grip the grip section 53, and to prevent the operator's hand from slipping.

These five surgical instruments 1 to 5 described above preferably have different grip sections 12, 23, 33, 44 and 53, respectively. Such different grip sections enable the operator to distinguish the surgical instruments.

To enable the grip sections of the surgical instruments to be distinguished, various methods can be used. For example, each of the grip sections may be changed in shape, size, material, texture or color, or each of the grip, sections may be marked with a different marker such as characters (numerals), symbols or graphical symbols.

For example, in the present embodiments shown in FIGS. 1 to 5, a portion indicated by A1 in the grip section 12, a portion indicated by A2 in the grip section 23, a portion indicated by A3 in the grip section 33, a portion indicated by A4 in the grip section (ejector bar grip section) 44, and a portion indicated by A5 in the grip section 53 may be marked either with different colors, or with different numerals.

In this way, the operator can readily distinguish the various surgical instruments simply by looking at each of the grip sections 12, 23, 33, 44, and 53 so as to prevent any instrument from being mistakenly used.

Further, when marking the portions A1 to A5 with different numerals, the numerals may be assigned to designate the surgical instruments in the order that they are used in the treatment of a vertebral body compression fracture, which facilitates the work of the operator.

Furthermore, in each of the surgical instruments 1 to 5, the grip sections 12, 23, 33, 44, and 53 maybe freely detachable from the other part of the instrument, respectively. In this case, the surgical instruments 1 to 5 may have a common grip section that can be replaceably used as the grip section of each instrument as required.

Hereinafter, description will be made with respect to one example of a method of using the set of surgical instruments.

<1> First, as shown in FIGS. 6(A) and 6(B), under X-ray guidance, a probe (a surgical instrument) is inserted via the vertebral arch 92 toward the targeted vertebral body 91 on each side of the vertebra 9. Consequently, on either side of the vertebra 9, paths 93, 93 are formed so as to pass though the vertebral arch 92 into the vertebral body 91. Each of the paths 93, 93 has a small diameter.

<2> Next, as shown in FIGS. 7(A) and 7(B), the operator grips the grip section 12 of the guide rod 1 to insert its distal end portion into one of the paths 93, to thereby widen one of the paths 93.

In this regard, it is to be noted that two or more guide rods 1 are prepared, in which each rod-shaped body 11 has a different outer diameter (e.g. three types of guide rods having an outer diameter of 4 mm, 5 mm, and 6 mm, respectively). By using these guide rods 1 in the order in which the outer diameter is increased, it is possible to widen the path 93 in multiple steps. Such an operation is performed on each of the paths 93 on the right and left sides.

<3> Next, as shown in FIGS. 8(A) and (B), the operator grips the grip section 23 of the vertical elevator 2 to insert the distal end portion of the vertical elevator 2, including the pushing section 22 and the distal end portion of the main body 21, into the vertebral body 91 through one of the paths 93 to position the pushing section 22 in the anterior portion of the vertebral body 91. At this time, the distal end surface 221 of the pushing section 22 is set so as to point in an upward direction.

Then, the proximal end portion of the main body 21 is pushed downwardly so that the distal end surface 221 of the pushing section 22 comes into contact with the upper anterior surface of the inside of the vertebral body 91, and so that the upper anterior portion of the vertebral body 91 is pushed. Consequently, the upper anterior portion of the vertebral body 91 is upwardly elevated.

When such an operation is complete, the distal end portion of the vertical elevator 2 is removed from the vertebra 9. Further, the operator again inserts the vertical elevator 2 into the vertebral body 91 through the other path 93 to perform the same operation as described above.

<4> Next, as shown in FIGS. 9(A) and 9(B), the operator grips the grip section 33 of the horizontal elevator 3 to insert the distal end portion of the horizontal elevator 3, including the pushing section 32 and the distal end portion of the main body 31, into the vertebral body 91 through one of the paths 93 to position the pushing section 32 in the middle portion of the vertebral body 91. At this time, one of the side surfaces 321 of the pushing section 32 is set so as to point in an upward direction.

Then, the proximal end of the main body 31 is pushed downwardly so that the side surface 321 of the pushing section 32 comes into contact with the upper middle surface of the inside of the vertebral body 91, and so that the upper middle portion of the vertebral body 91 is pushed. Consequently, the upper middle portion of the vertebral body 91 is upwardly elevated.

Further, the pushing section 32 is turned about an axis of the main body 31 by a prescribed angle, and then the same operation as described above is performed. In this way, it is possible to perform the reduction procedure on the upper middle portion of the vertebral body 91 over a wide range.

When such an operation is complete, the distal end portion of the horizontal elevator 3 is removed from the vertebra 9. Further, the operator again inserts the horizontal elevator 3 into the vertebral body 91 through the other path 93 to perform the same operation as described above.

Each of the reduction procedures described in <3> and <4> is repeatedly performed two or more times until the vertebral body 91 is returned to a substantially normal position.

In this regard, it is to be noted that the cavity 911 is created within the vertebral body 91 as a result of the reduction procedures.

<5> Next, as shown in FIGS. 10(A) and 10(B), the operator grips the tubular body grip section 42 of the tubular body 41 of the inserter 4 to insert the distal end portion of the tubular body 41 into the vertebral body 91 through one of the paths 93, so that the distal end of the tubular body 41 is positioned at a desired position within the cavity 911.

While the operator maintains a grip on the tubular body grip section 42 with one hand to maintain the position of the distal end of the tubular body 41 within the vertebral body 91, the filler 7 is fed into the lumen of the tubular body 41 from the proximal end of the tubular body grip section 42.

Then, the operator grips the ejector bar grip section 44 of the ejector bar 43 with the other hand to insert the ejector bar 43 into the lumen of the tubular body 41 from the proximal end of the tubular body grip section 42 toward the distal end of the tubular body 41. By doing so, the filler 7 filled in the lumen of the tubular body 41 is pushed by the distal end of the ejector bar 43 toward the distal end of the tubular body 41.

By further pushing the ejector bar 43 toward the distal end of the tubular body 41, the distal end of the ejector bar 43 projects out of the distal end of the tubular body 41 so that the filler 7 is inserted into the cavity 911.

In such an operation for inserting the filler 7 into the cavity 911, the maximum length of the ejector bar 43 projecting out from the distal end of the tubular body 41 is limited due to the abutment of the ejector bar grip section 44 with the tubular body grip section 42. Therefore, it is possible to prevent the ejector bar 43 from projecting out more than necessary, thereby preventing the ejector bar 43 from involuntarily pushing the vertebral body 91, and providing a high level of safety.

<6> Next, as shown in FIGS. 11(A) and 11(B), the operator grips the grip section 53 of the impactor 5 to insert the distal end portion of the impactor 5, including the impacting section 52 and the distal end portion of the main body 51, into the vertebral body 91 through one of the path 93.

Then, the filler 7 inserted in the cavity 911 in the operation described in <5> is impacted by the impacting section 52, thereby increasing the density (filling density) of the filler 7.

By repeatedly performing each of the operation for inserting the filler 7 described in <5> and the operation for increasing the density of the filler 7 described in <6> two or more times through each of the paths 93 on the right and left sides, the cavity created in the vertebral body 91 is filled with the filler 7 with being increased in a filling density.

By performing such operations described in <5> and <6>, the vertebral body 91 may be further reduced.

<7> Next, as shown in FIG. 12, each of the paths 93 on the right and left sides is sealed with a plug 8 made of a biomaterial such as hydroxyapatite or the like. By doing so, it is possible to prevent the filler 7 from leaking out of the inside of the vertebral body 91.(cavity 911) through the paths 93, 93. Therefore, it is possible to prevent the vertebral body 91 from being collapsed again.

In this regard, it is to be noted that each of the paths 93 is sealed with, for example, a bone cement or the like instead of the plug 8.

Once all of the surgical procedures for the treatment of a compression fracture of the vertebral body 91 are complete, the operation site (incision site) is closed by suturing or ligation to finish the surgical operation.

It is to be noted that, since each of the surgical instruments is provided with a scale, by utilizing the scale when performing the operations described in <2> to <6>, it is possible to prevent the distal end portion of each surgical instrument from being inserted more than necessary into the vertebral body 91 and involuntarily pushing the vertebral body 91. Therefore, each operation can be performed with a high level of safety.

Although the instrument for widening a working path, the instruments for reducing deformity, the instrument for inserting a filler, the instrument for impacting the inserted filler, and the set of surgical instruments according to the present invention have been described with reference to the illustrated embodiments, the present invention is not limited thereto.

Further, it is possible to make various changes and additions to each part of the instrument for widening a working path, the instruments for reducing deformity, the instrument for inserting a filler, and the instrument for impacting the inserted filler of the present invention, so long as the same functions are achieved.

Furthermore, a combination of the instruments in the set of surgical instruments is not limited to the combination in the present embodiment, so long as the set includes at least one instrument for reducing deformity. For example, in the present invention, any one or two or more instruments for widening a working path, for inserting a filler, and for impacting a filler may be eliminated from the set. Also, any surgical instrument may be added to the set.

As described above, according to the present invention, it is possible to perform surgical procedures for the treatment of vertebral body compression fractures easily and reliably. Further, since the surgical instruments according to the present invention have excellent operability and usability, it is possible to prevent operation mistakes and to shorten a time required for a surgical operation to be completed.

Furthermore, according to the present invention, surgical procedures for the treatment of vertebral body compression fractures are performed with a high level of safety and low invasiveness. This reduces a burden on a patient.

Finally, it is to be understood that many changes and additions may be made to the embodiments described above without departing from the scope and spirit of the invention as defined in the following claims.

Further, it is also to be understood that the present disclosure relates to subject matter contained in Japanese Patent Application No. 2001-373441 (filed on Dec. 6, 2001) which it expressly incorporated herein by reference in its entireties.

What is claimed is:

1. A set of surgical instruments for use in the treatment of vertebral body compression fractures comprising:

at least one first instrument configured to widen a working path formed in a collapsed vertebral body, the first instrument comprising a rod-shaped body having a distal end, a proximal end and a peripheral surface, and a grip section fixedly provided on the proximal end of the rod-shaped body, wherein the distal end portion of the rod-shaped body is configured to be inserted into the working path to increase its diameter;

at least one second instrument configured to be used in the treatment of vertebral body compression fractures to reduce deformity by returning the upper portion of a collapsed vertebral body to a substantially original shape, the second instrument to reduce deformity comprising: a rod-shaped main body having a distal end, a proximal end and a peripheral surface; a grip section fixedly provided on the proximal end of the main body; a pushing section integrally provided on the distal end of the main body, the pushing section being inclined with respect to the main body to push the upper portion of the collapsed vertebral body, wherein the angle of inclination between the pushing section of the instrument and the main body is constant and lies within the range of 5 to 15°; and a marker provided on the grip section to indicate a direction in which the pushing section is inclined;

a third instrument for inserting a filler into the vertebral body; the third instrument comprising a tubular body having a distal end, a proximal end and a peripheral surface, the tubular body having a lumen passing through the tubular body from the proximal end to the distal end, an ejector bar which is configured to be inserted into the lumen of the tubular body to eject a filler filled in the lumen, the ejector bar having a distal end and a proximal end, and a grip section which is fixedly provided on the proximal end of the ejector bar; and a fourth instrument for impacting the filler inserted in the vertebral body to a high density, the fourth instrument comprising a rod-shaped main body having a distal end, a proximal end and a peripheral surface, an impacting section provided on the distal end of the main body for impacting the filler, the impacting section having a distal end, and a grip section which is fixedly provided on the proximal end of the main body, wherein the grip sections of the first to fourth instruments are different from each other so that these instruments can be tactily identified by their grip sections.

2. The set of surgical instruments as claimed in claim 1, wherein the pushing section of the second instrument has a distal end surface that functions as the contact surface, and the distal end surface is formed with irregularities.

3. The set of surgical instruments as claimed in claim 2, wherein the upper portion of the vertebral body includes an upper anterior portion, and the second instrument is used to reduce the upper anterior portion of the vertebral body.

4. The set of surgical instruments as claimed in claim 1, wherein the length of a portion of the second instrument including the main body and the pushing section is in the range of 13 to 21 cm, in which the length of the pushing section is extremely shorter than that of the main body.

5. The set of surgical instruments as claimed in claim 1 wherein the distal end of the rod-shaped body of the first instrument has a rounded form.

6. The set of surgical instruments as claimed in claim 5, wherein the first instrument is adapted to be used by being inserted into the working path, and the rod-shaped body has a scale to indicate a depth of insertion of the first instrument into the working path, the scale extending in a longitudinal direction of the rod-shaped body along the peripheral surface thereof.

7. The set of surgical instruments as claimed in claim 1, wherein the pushing section of the second instrument has a contact surface which comes into contact with the upper surface of the inside of the vertebral body.

8. The set of surgical instruments as claimed in claim 7, wherein the contact surface is formed with irregularities to prevent or suppress slippage of the contact surface against the upper surface of the vertebral body.

9. The set of surgical instruments as claimed in claim 1, wherein the pushing section of the second instrument has a peripheral surface, and at least a part of the peripheral surface of the pushing section functions as the contact surface and a part of the peripheral surface is formed with irregularities.

10. The set of surgical instruments as claimed in claim 9, wherein the upper portion of the vertebral body includes an upper middle portion, and the second instrument is used to reduce the upper middle portion of the vertebral body.

11. The set of surgical instruments as claimed in claim 1, wherein the pushing section of the second instrument is formed into a flat shape.

12. The set of surgical instruments as claimed in claim 1, wherein the second instrument is adapted to be used by being inserted into the vertebral body through the working path formed in the vertebra, and the main body has a scale to indicate a depth of insertion of the second instrument into the vertebral body, the scale extending in a longitudinal direction of the main body along the peripheral surface thereof.

13. The set of surgical instruments as claimed in claim 1, wherein the outer diameter of the impacting section of the fourth instrument is gradually increased toward the distal end thereof.

14. The set of surgical instruments as claimed in claim 1, wherein the impacting section of the fourth instrument has a distal end surface formed with irregularities.

15. The set of surgical instruments as claimed in claim 1, wherein the impacting section of the fourth instrument is integrally formed with the main body.

16. The set of surgical instruments as claimed in claim 1, wherein the fourth instrument is adapted to be used by being inserted into the vertebral body through the working path formed in the vertebra, and the main body has a scale to indicate a depth of insertion of the fourth instrument into the vertebra, the scale extending in a longitudinal direction of the main body along the peripheral surface thereof.

17. The set of surgical instrument as claimed in claim 1, wherein the first to fourth instruments are configured to be used in this order in the treatment of vertebral body compression fractures.

18. The set of surgical instruments as claimed in claim 1, wherein said at least one first instrument includes two or more instruments to widen the working path, in which each rod-shaped body has a different outer diameter to gradually enlarge the diameter of the working path.

19. The set of surgical instruments as claimed in claim 1, wherein said at least one second instrument includes two or more different type instruments to be selectively used depending on a region to be reduced in the vertebral body.

* * * * *